United States Patent
Fischer et al.

(10) Patent No.: US 7,854,945 B2
(45) Date of Patent: Dec. 21, 2010

(54) FUNCTIONALIZED NANOTUBES

(75) Inventors: Alan Fischer, Cambridge, MA (US); Robert Hoch, Hensonville, NY (US); David Moy, Winchester, MA (US); Chun-Ming Niu, Somerville, MA (US); Naoya Ogata, Tokyo (JP); Howard Tennent, Kenneth Square, MA (US)

(73) Assignee: Hyperion Catalysis International, Inc., Cambridge, MA (US)

( * ) Notice: Subject to any disclaimer, the term of this patent is extended or adjusted under 35 U.S.C. 154(b) by 0 days.

(21) Appl. No.: 11/412,350

(22) Filed: Apr. 26, 2006

(65) Prior Publication Data

US 2006/0193868 A1    Aug. 31, 2006

Related U.S. Application Data

(62) Division of application No. 09/594,673, filed on Jun. 16, 2000, now abandoned, which is a division of application No. 08/352,400, filed on Dec. 8, 1994, now Pat. No. 6,203,814.

(51) Int. Cl.
| | |
|---|---|
| *D01F 9/12* | (2006.01) |
| *A61K 9/16* | (2006.01) |
| *A61K 9/50* | (2006.01) |
| *B05D 7/00* | (2006.01) |
| *A01K 1/015* | (2006.01) |
| *B32B 5/16* | (2006.01) |
| *D02G 3/00* | (2006.01) |

(52) U.S. Cl. ............... 424/491; 423/447.1; 427/212; 428/221; 428/323; 428/372

(58) Field of Classification Search ............. 424/443, 424/491; 423/460, 447.1; 427/2.31, 231, 427/212; 428/378, 221, 323, 372
See application file for complete search history.

(56) References Cited

U.S. PATENT DOCUMENTS

| | | | |
|---|---|---|---|
| 4,009,305 A | 2/1977 | Fujimaki et al. | |
| 4,645,297 A * | 2/1987 | Yoshihara et al. | 385/128 |
| 4,663,230 A | 5/1987 | Tennent | |
| 4,724,062 A * | 2/1988 | Naarmann et al. | 205/159 |
| 4,855,091 A | 8/1989 | Geus et al. | |
| 5,002,651 A * | 3/1991 | Shaw et al. | 204/400 |
| 5,110,833 A | 5/1992 | Mosbach | |
| 5,152,801 A | 10/1992 | Altermatt et al. | |
| 5,171,560 A | 12/1992 | Tennent | |
| 5,316,990 A | 5/1994 | Cooper et al. | |
| 5,424,054 A | 6/1995 | Bethune et al. | |
| 5,456,897 A | 10/1995 | Moy et al. | |
| 5,611,964 A | 3/1997 | Friend et al. | |
| 5,726,116 A | 3/1998 | Moy et al. | |
| 5,965,470 A | 10/1999 | Bening et al. | |
| 6,294,144 B1 | 9/2001 | Moy et al. | |

FOREIGN PATENT DOCUMENTS

| | | |
|---|---|---|
| JP | 59112068 A | 6/1984 |
| JP | 62079784 A | 4/1987 |
| JP | 2093032 A | 4/1990 |
| WO | 8707559 A1 | 12/1987 |
| WO | 8907163 A1 | 8/1989 |
| WO | 9101621 A2 | 2/1991 |
| WO | 9105089 A1 | 4/1991 |
| WO | 9319844 A1 | 10/1993 |
| WO | 9324687 A1 | 12/1993 |
| WO | 9507316 A1 | 3/1995 |
| WO | 9510481 A1 | 4/1995 |

OTHER PUBLICATIONS

Ebbesen RW and Ajayan P.M., "Large-Scale Synthesis of Carbon Nanotubes," Nature, 358 220, 1992.
Bening, R and McCarthy T. J., "Surface Chemistry of Fibrillar Carbon," Polymer Chem. 30 (1) 420, 1990.
Hoogenvaad, M.S., et al. "Metal Catalysts Supported on a Novel Carbon Support," Preparation of Catalysts VI, 263, 1995.
Anderson, G.W., et al., "The Use of Esters of N-Hydroxysuccinimide in Peptide Synthesis", J. Am. Chem. Soc, 86, pp. 1839-1842 (1964).
Cotton and Wilkinson, "Advanced Inorganic Chemistry", Wiley-Interscience Publication, New York 1980, p. 76.
Ebbesen et al., "Purification of Nanotubes," Nature 367: 519 (1994).
Fujiki, K., et al., "Radical Polymerization of Vinyl Monomers Initiated by Initiating Groups Introduced onto Carbon Black Surfaces," Polymer Preprints, Japan, vol. 38(6):1612-1614 (1989).
House, H., "Modern Synthetic Reactions," 2nd Ed., Benjamin/Cummings, Menlo Park, CA 1972, pp. 285-291.
Iijima, "Helical Microtubules of Graphitic Carbon," Nature 354:56-58 (1991).
March, J.P., "Advanced Organic Chemistry," 3rd Ed. Wiley-Interscience Publications, New York 1985, pp. 180-182.
March, J.P., "Advanced Organic Chemistry," 3rd Ed. Wiley-Interscience Publications, New York 1985, pp. 545.

(Continued)

*Primary Examiner*—Johann R Richter
*Assistant Examiner*—Luke E Karpinski

(57) ABSTRACT

Graphitic nanotubes, which includes tubular fullerenes (commonly called "buckytubes") and fibrils, which are functionalized by chemical substitution or by adsorption of functional moieties. More specifically the invention relates to graphitic nanotubes which are uniformly or non-uniformly substituted with chemical moieties or upon which certain cyclic compounds are adsorbed and to complex structures comprised of such functionalized fibrils linked to one another. The invention also relates to methods of introducing functional groups onto the surface of such fibrils.

12 Claims, No Drawings

OTHER PUBLICATIONS

Oberlin, A. & Endo, M., "Filamentous Growth of Carbon Through Benzene Decomposition," J. of Crystal Growth, vol. 32, pp. 335-349 (1976).

Ota, E., et al., "Existence and Reactivity of Acid Anhydride-Type Functional Groups on the Surface of Oxidizeded Carbon Fiber," Tanso (Carbon), 142:77-83 (1990).

Rodriguez, N., "A Review of Catalytically Grown Carbon Nanofibers," J. Mater. Research, vol. 8, pp. 3233-3250 (1993).

Scouten, W. H., "Solid Phase Biochemistry", Chemical Analysis, pp. 273-335 (1983).

Staab, H.A., "Synthesis Using Heterocyclic Amid (Azolides)," Angew, Chem. Internat. Edit. vol. 1(7):351-367, (1962).

Urry, G., "Anomalies in the Behavior of Graphite," Elementary Equilibrium Chemistry of Carbon, Wiley-Interscience Publication, New York (1989), pp. 25-29.

Weaver, J., "Totally Tubular," Science, 246: 611-612 (1994).

Zurer, P.S., "Supramolecular Chemistry Exploited to Build Nanotubes, Recognize DNA," Chemical & Engineering News, pp. 18-22 (1996).

Baker and Harris, Chemistry and Physics of Carbon, Walker and Thrower ed., vol. 14, 1978, p. 83.

* cited by examiner

FUNCTIONALIZED NANOTUBES

This application is a divisional of U.S. application Ser. No. 09/594,673, filed Jun. 16, 2000, which is a divisional of U.S. application Ser. No. 08/352,400, filed Dec. 8, 1994, now U.S. Pat. No. 6,203,814, all of which are hereby incorporated by reference in their entirety.

FIELD OF THE INVENTION

The invention relates broadly to graphitic nanotubes, which includes tubular fullerenes (commonly called "buckytubes") and fibrils, which are functionalized by chemical substitution or by adsorption of functional moieties. More specifically the invention relates to graphitic nanotubes which are uniformly or non-uniformly substituted with chemical moieties or upon which certain cyclic compounds are adsorbed and to complex structures comprised of such functionalized fibrils linked to one another. The invention also relates to methods of introducing functional groups onto the surface of such fibrils.

BACKGROUND OF THE INVENTION

This invention lies in the field of submicron graphitic fibrils, sometimes called vapor grown carbon fibers. Carbon fibrils are vermicular carbon deposits having diameters less than 1.0μ, preferably less than 0.5μ, and even more preferably less than 0.2μ. They exist in a variety of forms and have been prepared through the catalytic decomposition of various carbon-containing gases at metal surfaces. Such vermicular carbon deposits have been observed almost since the advent of electron microscopy. A good early survey and reference is found in Baker and Harris, *Chemistry and Physics of Carbon*, Walker and Thrower ed., Vol. 14, 1978, p. 83, hereby incorporated by reference. See also, Rodriguez, N., *J. Mater. Research*, Vol. 8, p. 3233 (1993), hereby incorporated by reference.

In 1976, Endo et al. (see Obelin, A. and Endo, M., *J. of Crystal Growth*, Vol. 32(1976), pp 335-349, hereby incorporated by reference) elucidated the basic mechanism by which such carbon fibrils grow. There were seen to originate from a metal catalyst particle, which, in the presence of a hydrocarbon containing gas, becomes supersaturated in carbon. A cylindrical ordered graphitic core is extruded which immediately, according to Endo et al., becomes coated with an outer layer of pyrolytically deposited graphite. These fibrils with a pyrolytic overcoat typically have diameters in excess of 0.1μ, more typically 0.2 to 0.5μ.

In 1983, Tennent, U.S. Pat. No. 4,663,230, hereby incorporated by reference, succeeded in growing cylindrical ordered graphite cores, uncontaminated with pyrolytic carbon. Thus, the Tennent invention provided access to smaller diameter fibrils, typically 35 to 700 Å (0.0035 to 0.070μ) and to an ordered, "as grown" graphitic surface. Fibrillar carbons of less perfect structure, but also without a pyrolytic carbon outer layer have also been grown.

The fibrils, buckytubes and nanofibers that are functionalized in this application are distinguishable from continuous carbon fibers commercially available as reinforcement materials. In contrast to fibrils, which have, desirably large, but unavoidably finite aspect ratios, continuous carbon fibers have aspect ratios (L/D) of at least $10^4$ and often $10^6$ or more. The diameter of continuous fibers is also far larger than that of fibrils, being always >1.0μ and typically 5 to 7μ.

Continuous carbon fibers are made by the pyrolysis of organic precursor fibers, usually rayon, polyacrylonitrile (PAN) and pitch. Thus, they may include heteroatoms within their structure. The graphitic nature of "as made" continuous carbon fibers varies, but they may be subjected to a subsequent graphitization step. Differences in degree of graphitization, orientation and crystallinity of graphite planes, if they are present, the potential presence of heteroatoms and even the absolute difference in substrate diameter make experience with continuous fibers poor predictors of nanofiber chemistry.

Tennent, U.S. Pat. No. 4,663,230 describes carbon fibrils that are free of a continuous thermal carbon overcoat and have multiple graphitic outer layers that are substantially parallel to the fibril axis. As such they may be characterized as having their c-axes, the axes which are perpendicular to the tangents of the curved layers of graphite, substantially perpendicular to their cylindrical axes. They generally have diameters no greater than 0.1μ and length to diameter ratios of at least 5. Desirably they are substantially free of a continuous thermal carbon overcoat, i.e., pyrolytically deposited carbon resulting from thermal cracking of the gas feed used to prepare them.

Tennent, et al., U.S. Pat. No. 5,171,560, hereby incorporated by reference, describes carbon fibrils free of thermal overcoat and having graphitic layers substantially parallel to the fibril axes such that the projection of said layers on said fibril axes extends for a distance of at least two fibril diameters. Typically, such fibrils are substantially cylindrical, graphitic nanotubes of substantially constant diameter and comprise cylindrical graphitic sheets whose c-axes are substantially perpendicular to their cylindrical axis. They are substantially free of pyrolytically deposited carbon, have a diameter less than 0.1μ and a length to diameter ratio of greater than 5. These fibrils are of primary interest in the invention.

Further details regarding the formation of carbon fibril aggregates may be found in the disclosure of Snyder et al., U.S. patent Application Ser. No. 149,573, filed Jan. 28, 1988, and PCT Application No. US89/00322, filed Jan. 28, 1989 ("Carbon Fibrils") WO 89/07163, and Moy et al., U.S. patent application Ser. No. 413,837 filed Sep. 28, 1989 and PCT Application No. US90/05498, filed Sep. 27, 1990 ("Fibril Aggregates and Method of Making Same") WO 91/05089, all of which are assigned to the same assignee as the invention here and are hereby incorporated by reference.

Moy et al., U.S. Ser. No. 07/887,307 filed May 22, 1992, hereby incorporated by reference, describes fibrils prepared as aggregates having various macroscopic morphologies (as determined by scanning electron microscopy) in which they are randomly entangled with each other to form entangled balls of fibrils resembling bird nests ("BN"); or as aggregates consisting of bundles of straight to slightly bent or kinked carbon fibrils having substantially the same relative orientation, and having the appearance of combed yarn ("CY") e.g., the longitudinal axis of each fibril (despite individual bends or kinks) extends in the same direction as that of the surrounding fibrils in the bundles; or, as, aggregates consisting of straight to slightly bent or kinked fibrils which are loosely entangled with each other to form an "open net" ("ON") structure. In open net structures the degree of fibril entanglement is greater than observed in the combed yarn aggregates (in which the individual fibrils have substantially the same relative orientation) but less than that of bird nests. CY and ON aggregates are more readily dispersed than BN making them useful in composite fabrication where uniform properties throughout the structure are desired.

When the projection of the graphitic layers on the fibril axis extends for a distance of less than two fibril diameters, the carbon planes of the graphitic nanofiber, in cross section, take on a herring bone appearance. These are termed fishbone fibrils. Geus, U.S. Pat. No. 4,855,091, hereby incorporated by reference, provides a procedure for preparation of fishbone fibrils substantially free of a pyrolytic overcoat. These fibrils are also useful in the practice-of the invention.

Carbon nanotubes of a morphology similar to the catalytically grown fibrils described above have been grown in a high temperature carbon arc (Iijima, Nature 354 56 1991). It is now generally accepted (Weaver, Science 265 1994) that these arc-grown nanofibers have the same morphology as the earlier catalytically grown fibrils of Tennent. Arc grown carbon nanofibers are also useful in the invention.

McCarthy et al., U.S. patent Application Serial No. 351, 967 filed May 15, 1989, hereby incorporated by reference, describes processes for oxidizing the surface of carbon fibrils that include contacting the fibrils with an oxidizing agent that includes sulfuric acid ($H_2SO_4$) and potassium chlorate ($KClO_3$) under reaction conditions (e.g., time, temperature, and pressure) sufficient to oxidize the surface of the fibril. The fibrils-oxidized according to the processes of McCarthy, et al. are non-uniformly oxidized, that is, the carbon atoms are substituted with a mixture of carboxyl, aldehyde, ketone, phenolic and other carbonyl groups.

Fibrils have also been oxidized non-uniformly by treatment with nitric acid. International Application PCT/US94/10168 discloses the formation of oxidized fibrils containing a mixture of functional groups. Hoogenvaad, M. S., et al. ("Metal Catalysts supported on a Novel Carbon Support", Presented at Sixth International Conference on Scientific Basis for the Preparation of Heterogeneous Catalysts, Brussels, Belgium, September 1994) also found it beneficial in the preparation of fibril-supported precious metals to first oxidize the fibril surface with nitric acid. Such pretreatment with acid is a standard step in the preparation of carbon-supported noble metal catalysts, where, given the usual sources of such carbon, it serves as much to clean the surface of undesirable materials as to functionalize it.

In published work, McCarthy and Bening (Polymer Preprints ACS Div. of Polymer Chem. 30 (1)420(1990)) prepared derivatives of oxidized fibrils in order to demonstrate that the surface comprised a variety of oxidized groups. The compounds they prepared, phenylhydrazones, haloaromaticesters, thallous salts, etc., were selected because of their analytical utility, being, for example, brightly colored, or exhibiting some other strong and easily identified and differentiated signal. These compounds were not isolated and are, unlike the derivatives described herein, of no practical significance.

While many uses have been found for carbon fibrils and aggregates of carbon fibrils, as described in the patents and patent applications referred to above, many different and important uses may be developed if the fibril surfaces are functionalized. Functionalization, either uniformly or non-uniformly, permits interaction of the functionalized fibrils with various substrates to form unique compositions of matter with unique properties and permits fibril structures to be created based on linkages between the functional sites on the fibrils' surfaces.

OBJECTS OF THE INVENTION

It is therefore a primary object of this invention to provide functionalized fibrils, i.e. fibrils whose surfaces are uniformly or non-uniformly modified so as to have a functional chemical moiety associated therewith.

It is a further and related object of this invention to provide fibrils whose surfaces are functionalized by reaction with oxidizing or other chemical media.

It is a further and related object of this invention to provide fibrils whose surfaces are uniformly modified either by chemical reaction or by physical absorption of species which themselves have a chemical reactivity.

It is a further object to provide fibrils whose surfaces have been modified e.g. by oxidation which are then further modified by reaction with functional groups.

It is still a further and related object of this invention to provide fibrils whose surfaces are modified with a spectrum of functional groups so that the fibrils can be chemically reacted or physically bonded to chemical groups in a variety of substrates.

It is still the further and related object of this invention to provide complex structures of fibrils by linking functional groups on the fibrils with one another by a range of linker chemistries.

It is still a further and related object of this invention to provide methods for chemical modification of fibril surfaces and methods for physically absorbing species on the surfaces of fibrils so as to provide, in each case, a functional moiety associated with the surface of the fibril.

It is yet a further object of this invention to provide new compositions of matter based upon the functionalized fibrils.

DETAILED DESCRIPTION OF THE INVENTION

These and other objects of the invention are achieved in compositions which broadly have the formula

where n is an integer, L is a number less than 0.1 n, m is a number less than 0.5 n, each of R is the same and is selected from $SO_3H$, COOH, $NH_2$, OH, CHO, CN, COCl, halide, COSH, SH, COOR', SR', $SiR'_3$, $Si$—$(OR')_y$$R'_{3-y}$, $Si$—$(O$—$SiR'_2$—$)OR'$, R'', Li, $AlR'_2$, Hg—X, $TlZ_2$ and Mg—X, y is an integer equal to or less than 3, R' is alkyl, aryl, cycloalkyl or aralkyl, R'' is fluoroalkyl, fluoroaryl, fluorocycloalkyl, fluoroaralkyl or cycloaryl, X is halide, and Z is carboxylate or trifluoroacetate.

The carbon atoms, $C_n$, are surface carbons of a substantially cylindrical, graphitic nanotube of substantially constant diameter. The nanotubes include those having a length to diameter ratio of greater than 5 and a diameter of less than 0.5µ, preferably less than 0.1µ. The nanotubes can also be substantially cylindrical, graphitic nanotubes which are substantially free of pyrolytically deposited carbon, more preferably those characterized by having a projection of the graphite layers on the fibril axis which extends for a distance of at least two fibril diameters and/or those having cylindrical graphitic sheets whose c-axes are substantially perpendicular to their cylindrical axis. These compositions are uniform in that each of R is the same.

Non-uniformly substituted nanotubes are also prepared. These include compositions of the formula

where n, L, m, R and the nanotube itself are as defined above, provided that each of R does not contain oxygen, or, if each of R is an oxygen-containing group COOH is not present.

Functionalized nanotubes having the formula $$[C_nH_L]R_m$$

where n, L, m, R and R' have the same meaning as above and the carbon atoms are surface carbon atoms of a fishbone fibril having a length to diameter ratio greater than 5, are also included within the invention. These may be uniformly or non-uniformly substituted. Preferably, the nanotubes are free of thermal overcoat and have diameters less than 0.5μ.

Also included in the invention are functionalized nanotubes having the formula $$[C_nH_L][R'\text{---}R]_m$$

where n, L, m, R' and R have the same meaning as above. The carbon atoms, $C_n$, are surface carbons of a substantially cylindrical, graphitic nanotube of substantially constant diameter. The nanotubes have a length to diameter ratio of greater than 5 and a diameter of less than 0.5μ, preferably less than 0.1. The nanotubes may be nanotubes which are substantially free of pyrolytically deposited carbon. More preferably, the nanotubes are those in which the projection of the graphite layers on the fibril axes extends for a distance of at least two fibril diameters and/or those having cylindrical graphitic sheets whose c-axes are substantially perpendicular to their cylindrical axis.

In both uniformly and non-uniformly substituted nanotubes, the surface atoms $C_n$ are reacted. Most carbon atoms in the surface layer of a graphitic fibril, as in graphite, are basal plane carbons. Basal plane carbons are relatively inert to chemical attack. At defect sites, where, for example, the graphitic plane fails to extend fully around the fibril, there are carbon atoms analogous to the edge carbon atoms of a graphite plane (See Urry, *Elementary Equilibrium Chemistry of Carbon*, Wiley, New York 1989.) for a discussion of edge and basal plane carbons).

At defect sites, edge or basal plane carbons of lower, interior layers of the nanotube may be exposed. The term surface carbon includes all the carbons, basal plane and edge, of the outermost layer of the nanotube, as well as carbons, both basal plane and/or edge, of lower layers that may be exposed at defect sites of the outermost layer. The edge carbons are reactive and must contain some heteroatom or group to satisfy carbon valency.

The substituted nanotubes described above may advantageously be further functionalized. Such compositions include compositions of the formula $$[C_nH_L]A_m$$

where the carbons are surface carbons of a nanotube, n, L and m are as described above, A is selected from
OY, NHY,

—CR'$_2$—OY, N=Y or C=Y,

Y is an appropriate functional group of a protein, a peptide, an enzyme, an antibody, a nucleotide, an oligonucleotide, an antigen, or an enzyme substrate, enzyme inhibitor or the transition-state analog of an enzyme substrate or is selected from R'—OH, R'—NH$_2$, R'SH, R'CHO, R'CN, R'X, R'SiR'$_3$, R'Si—(OR'—)$_y$R'$_{3-y}$, R'Si—(O—SiR'$_2$—)OR', R'—R", R'—N—CO, $(C_2H_4O)_w$H, $(C_3H_6O)_w$H, $(C_2H_4O)_w$—R', $(C_3H_6O)_w$—R' and R', and w is an integer greater than one and less than 200. The carbon atoms, $C_n$, are surface carbons of a substantially cylindrical, graphitic nanotube of substantially constant diameter. The nanotubes include those having a length to diameter ratio of greater than 5 and a diameter of less than 0.1μ, preferably less than 0.05μ. The nanotubes can also be substantially cylindrical, graphitic nanotubes which are substantially free of pyrolytically deposited carbon. More preferably they are characterized by having a projection of the graphite layers on the fibril axes which extends for a distance of at least two fibril diameters and/or they are comprised of cylindrical graphitic sheets whose c-axes are substantially perpendicular to their cylindrical axes. Preferably, the nanotubes are free of thermal overcoat and have diameters less than 0.5μ.

The functional nanotubes of structure $$[C_nH_L][R'\text{---}R]_m$$

may also be functionalized to produce compositions having the formula $$[C_nH_L][R'\text{---}A]_m$$

where n, L, m, R' and A are as defined above. The carbon atoms, $C_n$, are surface carbons of a substantially cylindrical, graphitic nanotube of substantially constant diameter. The nanotubes include those having a length to diameter ratio of greater than 5 and a diameter of less than 0.5μ, preferably less than 0.1μ. The nanotubes can also be substantially cylindrical, graphitic nanotubes which are substantially free of pyrolytically deposited carbon. More preferably they are characterized by having a projection of the graphite layers on the fibril axes which extends for a distance of at least two fibril diameters and/or by having cylindrical graphitic sheets whose c-axes are substantially perpendicular to their cylindrical axis. Preferably, the nanotubes are free of thermal overcoat and have diameters less than 0.5μ.

The compositions of the invention also include nanotubes upon which certain cyclic compounds are adsorbed. These include compositions of matter of the formula $$[C_nH_L][X\text{---}R_a]_m$$

where n is an integer, L is a number less than 0.1n, m is less than 0.5n, a is zero or a number less than 10, X is a polynuclear aromatic, polyheteronuclear aromatic or metallopolyheteronuclear aromatic moiety and R is as recited above. The carbon atoms, $C_n$, are surface carbons of a substantially cylindrical, graphitic nanotube of substantially constant diameter. The nanotubes include those having a length to diameter ratio of greater than 5 and a diameter of less than 0.5μ, preferably less than 0.1μ. The nanotubes can also be substantially cylindrical, graphitic nanotubes which are substantially free of pyrolytically deposited carbon and more preferably those characterized by having a projection of the graphite layers on said fibril axes which extend for a distance of at least two fibril diameters and/or those having cylindrical graphitic sheets whose c-axes are substantially perpendicular to their cylindrical axes. Preferably, the nanotubes are free of thermal overcoat and have diameters less than 0.5μ.

Preferred cyclic compounds are planar macrocycles as described on p. 76 of Cotton and Wilkinson, *Advanced organic. Chemistry*. More preferred cyclic compounds for adsorption are porphyrins and phthalocyanines.

The adsorbed cyclic compounds may be functionalized. Such compositions include compounds of the formula $$[C_nH_L][(X—A_a]_m$$

where m, n, L, a, X and A are as defined above and the carbons are surface carbons of a substantially cylindrical graphitic nanotube as described above.

The carbon fibrils functionalized as described above may be incorporated in a matrix. Preferably, the matrix is an organic polymer (e.g., a thermoset resin such as epoxy, bis-maleimide, polyamide, or polyester resin; a thermoplastic resin; a reaction injection molded resin; or an elastomer such as natural rubber, styrene-butadiene rubber, or cis-1,4-polybutadiene); an inorganic polymer (e.g., a polymeric inorganic oxide such as glass), a metal (e.g., lead or copper), or a ceramic material (e.g., Portland cement).

Without being bound to a particular theory, the functionalized fibrils are better dispersed into polymer systems because the modified surface properties are more compatible with the polymer, or, because the modified functional groups (particularly hydroxyl or amine groups) are bonded directly to the polymer as terminal groups. In this way, polymer systems such as polycarbonates, polyurethanes, polyesters or polyamides/imides bond directly to the fibrils making the fibrils easier to disperse with improved adherence.

The invention is also in methods of introducing functional groups onto the surface of carbon fibrils by contacting carbon fibrils with a strong oxidizing agent for a period of time sufficient to oxidize the surface of said fibrils and further contacting said fibrils with a reactant suitable for adding a functional group to the oxidized surface. In a preferred embodiment of the invention, the oxidizing agent is comprised of a solution of an alkali metal chlorate in a strong acid. In other embodiments of the invention the alkali metal chlorate is sodium chlorate or potassium chlorate. In preferred embodiments the strong acid used is sulfuric acid. Periods of time sufficient for oxidation are from about 0.5 hours to about 24 hours.

The invention is also in methods for producing a network of carbon fibrils comprising contacting carbon fibrils with an oxidizing agent for a period of time sufficient to oxidize the surface of the carbon fibrils, contacting the surface-oxidized carbon fibrils with reactant suitable for adding a functional group to the surface of the carbon fibrils, and further contacting the surface-functionalized fibrils with a cross-linking agent effective for producing a network of carbon fibrils. A preferred cross-linking agent is a polyol, polyamine or polycarboxylic acid.

Functionalized fibrils also are useful for preparing rigid networks of fibrils. A well-dispersed, three-dimensional network of acid-functionalized fibrils may, for example, be stabilized by cross-linking the acid groups (inter-fibril) with polyols or polyamines to form a rigid network.

The invention also includes three-dimensional networks formed by linking functionalized fibrils of the invention. These complexes include at least two functionalized fibrils linked by one or more linkers comprising a direct bond or chemical moiety. These networks comprise porous media of remarkably uniform equivalent pore size. They are useful as adsorbents, catalyst supports and separation media.

Although the interstices between these fibrils are irregular in both size and shape, they can be thought of as pores and characterized by the methods used to characterize porous media. The size of the interstices in such networks can be controlled by the concentration and level of dispersion of fibrils, and the concentration and chain lengths of the cross-linking agents. Such materials can act as structured catalyst supports and may be tailored to exclude or include molecules of a certain size. Aside from conventional industrial catalysis, they have special applications as large pore supports for biocatalysts.

The rigid networks can also serve as the backbone in biomimetic systems for molecular recognition. Such systems have been described in U.S. Pat. No. 5,110,833 and International Patent Publication No. WO93/19844. The appropriate choices for cross-linkers and complexing agents allow for stabilization of specific molecular frameworks.

Methods of Functionalizing Fibrils

The uniformly functionalized fibrils of the invention can be directly prepared by sulfonation, electrophilic addition to deoxygenated fibril surfaces or metallation. When arc grown nanofibers are used, they may require extensive purification prior to functionalization. Ebbesen et al. (Nature 367 519 (1994)) give a procedure for such purification.

Preferably, the carbon fibrils are processed prior to contacting them with the functionalizing agent. Such processing may include dispersing the fibrils in a solvent. In some instances the carbon fibrils may then be filtered and dried prior to further contact.

1. Sulfonation

Background techniques are described in March, J. P., *Advanced organic Chemistry*, 3rd Ed. Wiley, New York 1985; House, H., *Modern Synthetic Reactions*, 2nd Ed., Benjamin/Cummings, Menlo Park, Calif. 1972.

Activated C—H (including aromatic C—H) bonds can be sulfonated using fuming sulfuric acid (oleum), which is a solution of conc. sulfuric acid containing up to 20% $SO_3$. The conventional method is via liquid phase at T~80° C. using oleum; however, activated C—H bonds can also be sulfonated using $SO_3$ in inert, aprotic solvents, or $SO_3$ in the vapor phase. The reaction is:

—C—H+SO$_3$→—C—SO$_3$H

Over-reaction results in formation of sulfones, according to the reaction:

—C—H+SO$_3$→—C—SO$_2$—C—+H$_2$O         2.

EXAMPLE 1

Activation of C—H Bonds Using Sulfuric Acid

Reactions were carried out in the gas phase and in solution without any significant difference in results. The vapor phase reaction was carried out in a horizontal quartz tube reactor heated by a Lindberg furnace. A multi-neck flask containing 20% $SO_3$ in conc. $H_2SO_4$ fitted with gas inlet/outlet tubes was used as the $SO_3$ source.

A weighed sample of fibrils (BN or CC) in a porcelain boat was placed in the 1" tube fitted with a gas inlet; the outlet was connected to a conc. $H_2SO_4$ bubbler trap. Argon was flushed through the reactor for 20 min to remove all air, and the sample was heated to 300° C. for 1 hour to remove residual moisture. After drying, the temperature was adjusted to reaction temperature under argon.

When the desired temperature was stabilized, the $SO_3$ source was connected to the reactor tube and an argon stream was used to carry $SO_3$ vapors into the quartz tube reactor. Reaction was carried out for the desired time at the desired temperature, after which the reactor was cooled under flowing argon. The fibrils were then dried at 90° C. at 5" Hg vacuum to obtain the dry weight gain. Sulfonic acid (—SO$_3$H) content was determined by reaction with 0.100N NaOH and back-titration with 0.100N HCl using pH 6.0 as the end point.

The liquid phase reaction was carried out in conc. sulfuric acid containing 20% SO$_3$ in a multi-neck 100 cc flask fitted with a thermometer/temperature controller and a magnetic stirrer. A fibril slurry in conc. H$_2$SO$_4$ (50) was placed in the flask. The oleum solution (20 cc) was preheated to ~60° C. before addition to the reactor. After reaction, the acid-slurry was poured onto cracked ice, and diluted immediately with 1 l DI water. The solids were filtered and washed exhaustively with DI water until there was no change in pH of the wash effluent. Fibrils were dried at 100° C. at 5" Hg vacuum. Due to transfer losses on filtration, accurate weight gains could not be obtained. Results are listed in Table 1.

TABLE I

Summary of Reactions

| EX. | RUN # | REACT | SAMPLE Wt. g | FIBRIL TYPE | T °C. | TIME | DRY Wt GAIN | SO$_3$H CONC meq/g |
|---|---|---|---|---|---|---|---|---|
| 1A | 118-60A | Vap | 0.20 | CY | 110 | 15 m | 9.3% | 0.50 |
| 1B | 118-61A | Vap | 0.20 | BN | 100 | 30 m | 8.5% | 0.31 |
| 1C | 118-61B | Vap | 0.20 | BN | 65 | 15 m | 4.2% | 0.45 |
| 1D | 118-56A | Liq | 1.2 | CY | 50 | 10 m | | 0.33 |
| 1E | 118-56B | Liq | 1.0 | CY | 25 | 20 m | | 0.40 |

There was no significant difference in sulfonic acid content by reaction in the vapor phase or liquid phase. There was a temperature effect. Higher temperature of reaction (vapor phase) gives higher amounts of sulfones. In 118-61B, the 4.2% wt gain agreed with the sulfonic acid content (theoretical was 0.51 meq/g). Runs 60A and 61A had too high a wt gain to be accounted for solely by sulfonic acid content. It was therefore assumed that appreciable amounts of sulfones were also made.

2. Additions to Oxide-Free Fibril Surfaces

Background techniques are described in Urry, G., *Elementary Equilibrium Chemistry of Carbon*, Wiley, New York 1989.

The surface carbons in fibrils behave like graphite, i.e., they are arranged in hexagonal sheets containing both basal plane and edge carbons. While basal plane carbons are relatively inert to chemical attack, edge carbons are reactive and must contain some heteroatom or group to satisfy carbon valency. Fibrils also have surface defect sites which are basically edge carbons and contain heteroatoms or groups.

The most common heteroatoms attached to surface carbons of fibrils are hydrogen, the predominant gaseous component during manufacture; oxygen, due to its high reactivity and because traces of it are very difficult to avoid; and H$_2$O, which is always present due to the catalyst. Pyrolysis at ~1000° C. in a vacuum will deoxygenate the surface in a complex reaction with unknown mechanism, but with known stoichiometry. The products are CO and CO$_2$, in a 2:1 ratio. The resulting fibril surface contains radicals in a C$_1$-C$_4$ alignment which are very reactive to activated olefins. The surface is stable in a vacuum or in the presence of an inert gas, but retains its high reactivity until exposed to a reactive gas. Thus, fibrils can be pyrolized at ~1000° C. in vacuum or inert atmosphere, cooled under these same conditions and reacted with an appropriate molecule at lower temperature to give a stable functional group. Typical examples are:

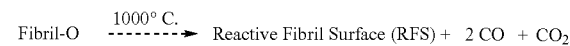

followed by:

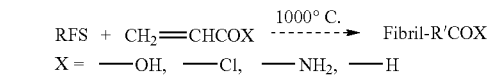

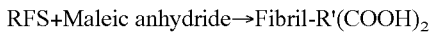
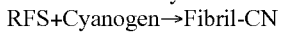

RFS+Maleic anhydride→Fibril-R'(COOH)$_2$
RFS+Cyanogen→Fibril-CN

RFS+CH$_2$=CH—CH$_2$X→Fibril-R'CH$_2$X       X=—NH$_2$, —OH, -Halogen,

RFS+H$_2$O→Fibril=O (quinoidal)

RFS+CH$_2$=CHCHO→Fibril-R'CHO (aldehydic)

RFS+CH$_2$=CH—CN→Fibril-R'CN where R' is a hydrocarbon radical (alkyl, cycloalkyl, etc.)

EXAMPLE 2

Preparation of Functionalized Fibrils by Reacting Acrylic Acid with Oxide-Free Fibril Surfaces One gram of BN fibrils in a porcelain boat is placed in a horizontal 1" quartz tube fitted with a thermocouple and situated in a Lindberg tube furnace. The ends are fitted with a gas inlet/outlets. The tube is purged with dry, deoxygenated argon for 10 minutes, after which the temperature of the furnace is raised to 300° C. and held for 30 minutes. Thereafter, under a continued flow of argon, the temperature is raised in 100° C. increments to 1000° C., and held there for 16 hours. At the end of that time, the tube is cooled to room temperature (RT) under flowing argon. The flow of argon is then shunted to pass through a multi-neck flask containing neat purified acrylic acid at 50° C. and fitted with gas inlet/outlets. The flow of acrylic acid/argon vapors is continued at RT for 6 hours. At the end of that time, residual unreacted acrylic acid is removed, first by purging with argon, then by vacuum drying at 100° C. at <5' vacuum. The carboxylic acid content is determined by reaction with excess 0.100N NaOH and back-titrating with 0.100N HCl to an endpoint at pH 7.5.

EXAMPLE 3

Preparation of Functionalized Fibrils by Reacting Acrylic Acid with Oxide-Free Fibril Surfaces The procedure is repeated in a similar manner to the above procedure, except that the pyrolysis and cool-down are carried out at $10^{-4}$ Torr vacuum. Purified acrylic acid vapors are diluted with argon as in the previous procedure.

EXAMPLE 4

Preparation of Functionalized Fibrils by Reacting Maleic Acid with Oxide-Free Fibril Surfaces The procedure is repeated as in Ex.2, except that the reactant at RT is purified maleic anhydride (MAN) which is fed to the reactor by passing argon-gas through a molten MAN bath at 80° C.

EXAMPLE 5

Preparation of Functionalized Fibrils by Reacting Acryloyl Chloride with Oxide-Free Fibril Surfaces The procedure is repeated as in Ex.2, except that the reactant at RT is purified acryloyl chloride, which is fed to the reactor by passing argon over neat acryloyl chloride at 25° C. Acid chloride content is determined by reaction with excess 0.100N NaOH and back-titration with 0.100N HCl.

Pyrolysis of fibrils in vacuum deoxygenates the fibril surface. In a TGA apparatus, pyrolysis at 1000° C. either in vacuum or in a purified Ar flow gives an average wt loss of 3% for 3 samples of BN fibrils. Gas chromatographic analyses detected only CO and $CO_2$, in ~2:1 ratio, respectively. The resulting surface is very reactive and activated olefins such as acrylic acid, acryloyl chloride, acrylamide, acrolein, maleic anhydride, allyl amine, allyl alcohol or allyl halides will react even at room temperature to form clean products containing only that functionality bonded to the activated olefin. Thus, surfaces containing only carboxylic acids are available by reaction with acrylic acid or maleic anhydride; surf only acid chloride by reaction with acryloyl chloride; only aldehyde from acrolein; only hydroxyl from allyl alcohol; only amine from allyl amine, and only halide from allyl halide.

3. Metallation

Background techniques are given in March, *Advanced Organic Chemistry*, 3rd ed., p 545

Aromatic C—H bonds can be metallated with a variety of organometallic reagents to produce carbon-metal bonds (C-M). M is usually Li, Be, Mg, Al, or Tl; however, other metals can also be used. The simplest reaction is by direct displacement of hydrogen in activated aromatics:

1. Fibril-H+R—Li→Fibril-Li+RH

The reaction may require additionally, a strong base, such as potassium t-butoxide or chelating diamines. Aprotic solvents are necessary (paraffins, benzene).

2. Fibril-H+AlR$_3$→Fibril-AlR$_2$+RH
3. Fibril-H+Tl(TFA)$_3$→Fibril-Tl(TFA)$_2$+HTFA
   TFA=Trifluoroacetate HTFA=Trifluoroacetic acid The metallated derivatives are examples of primary singly-functionalized fibrils. However, they can be reacted further to give other primary singly-functionalized fibrils. Some reactions can be carried out sequentially in the same apparatus without isolation of intermediates.

4. Fibril-M+$O_2$→Fibril-OH+MO M=Li, Al

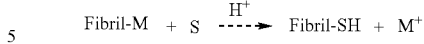

Fibril-M+$X_2$→Fibril-X+MX X=Halogen

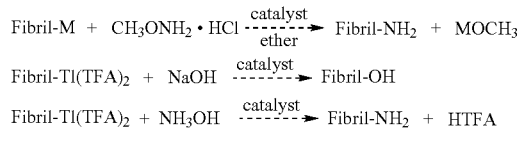

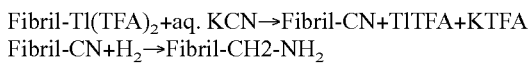

Fibril-Tl(TFA)$_2$+aq. KCN→Fibril-CN+TlTFA+KTFA
Fibril-CN+$H_2$→Fibril-CH2-NH$_2$

EXAMPLE 6

Preparation of Fibril-Li

One-gram of-CC fibrils is placed in a porcelain boat and inserted into a 1" quartz tube reactor which is enclosed in a Lindberg tube furnace. The ends of the tube are fitted with gas inlet/outlets. Under continuous flow of $H_2$, the fibrils are heated to 700° C. for 2 hours to convert any surface oxygenates to C—H bonds. The reactor is then cooled to RT under flowing $H_2$.

The hydrogenated fibrils are transferred with dry, de-oxygenated heptane (with LiAlH$_4$) to a 0.1 liter multi-neck round bottom flask equipped with a purified argon purging system to remove all air and maintain an inert atmosphere, a condenser, a magnetic stirrer and rubber septum through which liquids can be added by a syringe. Under an argon atmosphere, a 2% solution containing 5 mmol butyllithium in heptane is added by syringe and the slurry stirred under gentle reflux for 4 hours. At the end of that time, the fibrils are separated by gravity filtration in an argon atmosphere glove box and washed several times on the filter with dry, deoxygenated heptane. Fibrils are transferred to a 50 cc r.b. flask fitted with a stopcock and dried under $10^{-4}$ torr vacuum at 50° C. The lithium concentration is determined by reaction of a sample of fibrils with excess 0.100N HCl in DI water and back-titration with 0.100N NaOH to an endpoint at pH 5.0.

EXAMPLE 7

Preparation of Fibril-Tl(TFA)$_2$

One gram of CC fibrils are hydrogenated as in Ex. 5 and loaded into the multi-neck flask with HTFA which has been degassed by repeated purging with dry argon. A 5% solution of 5 mmol Tl(TFA)$_3$ in HTFA is added to the flask through the rubber septum and the slurry is stirred at gentle reflux for 6 hours. After reaction, the fibrils are collected and dried as in Ex. 1.

EXAMPLE 8

Preparation of Fibril-OH (Oxygenated Derivative Containing only OH Functionalization)

One half g of lithiated fibrils prepared in Ex. 6 are transferred with dry, deoxygenated heptane in an argon-atmosphere glove bag to a 50 cc single neck flask fitted with a stopcock and magnetic stirring bar. The flask is removed from the glove bag and stirred on a magnetic stirrer. The stopcock is then opened to the air and the slurry stirred for 24 hours. At the end of that time, the fibrils are separated by filtration and washed with aqueous MeOH, and dried at 50° C. at 5" vacuum. The concentration of OH groups is determined by reaction with a standardized solution of acetic anhydride in dioxane (0.252 M) at 80° C. to convert the OH groups to acetate esters, in so doing, releasing 1 equivalent of acetic acid/mole of anhydride reacted. The total acid content, free acetic acid and unreacted acetic anhydride, is determined by titration with 0.100N NaOH to an endpoint at pH 7.5.

EXAMPLE 9

Preparation of Fibril-$NH_2$

One gram of thallated fibrils is prepared as in Ex. 7. The fibrils are slurried in dioxane and 0.5 g triphenyl phosphine dissolved in dioxane is added. The slurry is stirred at 50° C. for several minutes, followed by addition at 50° C. of gaseous ammonia for 30 min. The fibrils are then separated by filtration, washed in dioxane, then DI water and dried at 80° C. at 5" vacuum. The amine concentration is determined by reaction with excess acetic anhydride and back-titration of free acetic acid and unreacted anhydride with 0.100N NaOH.

4. Derivatized Polynuclear Aromatic, Polyheteronuclear Aromatic and Planar Macrocyclic Compounds The graphitic surfaces of fibrils allow for physical adsorption of aromatic compounds. The attraction is through van der Waals forces. These forces are considerable between multi-ring heteronuclear aromatic compounds and the basal plane carbons of graphitic surfaces. Desorption may occur under conditions where competitive surface adsorption is possible or where the adsorbate has high solubility.

EXAMPLE 10

Adsorption of Porphyrins and Phthalocyanines onto Fibrils

The preferred compounds for physical adsorption on fibrils are derivatized porphyrins or phthalocyanines which are known to adsorb strongly on graphite or carbon blacks. Several compounds are available, e.g., a tetracarboxyiic acid porphyrin, cobalt (II) phthalocyanine or dilithium phthalocyanine. The latter two can be derivatized to a carboxylic acid form.

The loading capacity of the porphyrin or phthalocyanines can be determined by decoloration of solutions when they are added incrementally. The deep colors of the solutions (deep pink for the tetracarboxylic acid porphyrin in MeOH, dark blue-green for the Co(II) or the dilithium phthalocyanine in acetone or pyridine) are discharged as the molecules are removed by adsorption onto the black surface of the fibrils.

Loading capacities were estimated by this method and the footprints of the derivatives were calculated from their approximate measurements (~140 sq. Angstroms). For an average surface area for fibrils of 250 $m^2$/g, maximum loading will be ~0.3 mmol/g.

The tetracarboxylic acid porphyrin was analyzed by titration. The integrity of the adsorption was tested by color release in aqueous systems at ambient and elevated temperatures.

The fibril slurries were initially mixed (Waring blender) and stirred during loading. Some of the slurries were ultra-sounded after color was no longer discharged, but with no effect.

After loading, Runs 169-11, -12, -14 and -19-1 (see Table II) were washed in the same solvent to remove occluded pigment. All gave a continuous faint tint in the wash effluent, so it was difficult to determine the saturation point precisely. Runs 168-18 and -19-2 used the calculated amounts of pigment for loading and were washed only very lightly after loading.

The tetracarboxylic acid porphyrin (from acetone) and the Co phthalocyanine (from pyridine) were loaded onto fibrils for further characterization (Runs 169-18 and -19-2, respectively).

Analysis of Tetracarboxylic Acid Porphyrin

Addition of excess base (pH 11-12) caused an immediate pink coloration in the titrating slurry. While this did not interfere with the titration, it showed that at high pH, porphyrin desorbed. The carboxylic acid concentration was determined by back titration of excess NaOH using Ph 7.5 as end-point. The titration gave a loading of 1.10 meq/g of acid, equivalent to 0.275 meq/g porphyrin.

Analysis of Cobalt or Dilithium Phthalocyanine

The concentrations of these adsorbates were estimated from decoloration experiments only. The point where the blue-green tint did not fade after 30 min was taken as the saturation-point.

A number of substituted polynuclear aromatic or polyheteronuclear aromatic compounds were adsorbed on fibril surfaces. For adhesion, the number of aromatic rings should be greater than two per rings/pendant functional group. Thus, substituted anthracenes, phenanthrenes, etc., containing three fused rings, or polyfuntional derivatives containing four or more fused rings can be used in place of the porphyrin or phthalocayanine derivatives. Likewise, substituted aromatic heterocycles such as the quinolines, or multiply substituted heteroaromatics containing four or more rings can be used.

Table II summarizes the results of the loading experiments for the three porphyrin/phthalocyanine derivatives.

TABLE II

Summary of Adsorption Runs

| EX. | RUN # | Adsorbate | Wgt. Fib, g | Solv. | Loading g/g | Form | meq/g Titration |
|---|---|---|---|---|---|---|---|
| 10A | 169-11 | TCAPorph | 19.6 mg | Acet | 0.18 g/g | Acid | na |
| 10B | 169-12 | TCAPorph | 33.3 mg | $H_2O$ | 0.11 | Na Salt | na |
| 10C | 169-14 | DiLiPhth | 119.0 mg | Acet | 0.170 | Li | na |
| 10D | 169-19-1 | CoPhth | 250.0 mg | Pyr | 0.187 | Co | 0.335 (cal) |
| 10E | 169-18 | TCAPorph | 1.00 g | Acet | 0.205 | Acid | 1.10 (T) |
| 10F | 169-19-2 | CoPhth | 1.40 g | Pyr | 0.172 | Co | 0.303 (cal) |

TCAPorph = Tetracarboxylic Acid Porphyrin
DiLiPhth = Dilithium Phthalocyanine
CoPhth = Cobalt (II) Phthalocyanine
(cal) = calculated
(T) = Titration 5. Chlorate or Nitric Acid Oxidation Literature on the oxidation of graphite by strong oxidants such as potassium chlorate in conc. sulfuric acid or nitric acid, includes R. N. Smith, *Quarterly Review* 13, 287 (1959); M. J. D. Low, *Chem. Rev.* 60, 267 (1960)). Generally, edge carbons (including defect sites) are attacked to give mixtures of carboxylic acids, phenols and other oxygenated groups. The mechanism is complex involving radical reactions.

EXAMPLE 11

Preparation of Carboxylic Acid-Functionalized Fibrils Using Chlorate

The sample of CC fibrils was slurried in conc. $H_2SO_4$ by mixing with a spatula and then transferred to a reactor flask fitted with gas inlet/outlets and an overhead stirrer. With stirring and under a slow flow of argon, the charge of $NaClO_3$ was added in portions at RT over the duration of the run.

Chlorine vapors were generated during the entire course of the run and were swept out of the reactor into a aqueous NaOH trap. At the end of the run, the fibril slurry was poured over cracked ice and vacuum filtered. The filter cake was then transferred to a Soxhlet thimble and washed in a Soxhlet extractor with DI water, exchanging fresh water every several hours. Washing was continued until a sample of fibrils, when added to fresh DI water, did not change the pH of the water. The fibrils were then separated by filtration and dried at 100° C. at 5" vacuum overnight.

The carboxylic acid content was determined by reacting a sample with excess 0.100N NaOH and back-titrating with 0.100" HCl to an endpoint at pH 7.5. The results are listed in the Table.

TABLE III

Summary of Direct Oxidation Runs

| Acid, Ex. | RUN # | Fibrils | Components, g NaClO$_3$ | cc H$_2$SO$_4$ | Time hours | Wash Ph | Rec Wgt | meq/g |
|---|---|---|---|---|---|---|---|---|
| 11A | 168-30 | 10.0 | 8.68 | 450 | 24 | 5.7 | 10.0 | 0.78 |
| 11B | 168-36 | 12.0 | 13.9 | 600 | 24 | 5.9 | 13.7 | 0.75 |

EXAMPLE 12

Preparation of Carboxylic Acid-Functionalized Fibrils Using Nitric Acid

A weighed sample of fibrils was slurried with nitric acid of the appropriate strength in a bound bottom multi-neck indented reactor flask equipped with an overhead stirrer and a water condenser. With constant stirring, the temperature was adjusted and the reaction carried out for the specified time. Brown fumes were liberated shortly after the temperature exceeded 70° C., regardless of acid strength. After the reaction, the slurry was poured onto cracked ice and diluted with DI water. The slurry was filtered and excess acid removed by washing in a Soxhlet extractor, replacing the reservoir with fresh DI water every several hours, until a slurried sample gave no change in Ph from DI water. The fibrils were dried at 100° C. at 5" vacuum overnight. A weighed portion of fibrils was reacted with standard 0.100 N NaOH and the carboxylic acid content determined by back-titration with 0.100 N HCl. Surface oxygen content was determined by XPS. Dispersibility in water was tested at 0.1 wt % by mixing in a Waring Blender at high for 2 min. Results are summarized in Table 4.

TABLE IV

Summary of Direct Oxidation Runs

| | COMPONENTS | | | | | | ESCA, at % | | |
|---|---|---|---|---|---|---|---|---|---|
| Ex. | Gms. Fibrils | cc Acid | Acid Conc. | Temp. °C. | Time | Wgt. Loss | COOH meq/g | C | O | Disp H$_2$O |
| 12A | 1 (BN) | 300 | 70% | RT | 24 hr | 0 | <0.1 | 98 | 2 | P |
| 12B | 1 (BN) | 300 | 15 | rflx | 48 | <5% | <0.1 | not analyzed | | P |
| 12C | 20 (BN) | 1.0 l | 70 | rflx | 7 | 25% | 0.8 | not analyzed | | G |
| 12D | 48 (BN) | 1.0 l | 70 | rflx | 7 | 20% | 0.9 | not analyzed | | G |

P = Poor;
G = Good

6. Secondary Derivatives of Functionalized Fibrils

Carboxylic Acid-functionalized Fibrils

The number of secondary derivatives which can be prepared from just carboxylic acid is essentially limitless. Alcohols or amines are easily linked to acid to give stable esters or amides. If the alcohol or amine is part of a di- or polyfunctional molecule, then linkage through the O— or NH— leaves the other functionalities as pendant groups. Typical examples of secondary reagents are:

| GENERAL FORMULA | PENDANT GROUP | EXAMPLES |
|---|---|---|
| HO—R, R = alkyl, aralkyl, aryl, fluoroethanol, polymer, SiR'$_3$ | R— | Methanol, phenol, trifluorocarbon, OH-terminated Polyester, silanols |
| H$_2$N—R R = same as above | R— | Amines, anilines, fluorinated amines, silylamines, amine terminated polyamides |
| Cl—SiR$_3$ | SiR$_3$— | Chlorosilanes |
| HO—R—OH, R = alkyl, aralkyl, CH$_2$O— | HO— | Ethyleneglycol, PEG, Pentaerythritol, bis-Phenol A |
| H$_2$N—R—NH$_2$, R = alkyl, aralkyl | H$_2$N— | Ethylenediamine, polyethyleneamines |
| X—R—Y, R = alkyl, etc; X = OH or NH$_2$; Y = SH, CN, C = O, CHO, alkene, alkyne, aromatic, heterocycles | Y— | Polyamine amides, Mercaptoethanol |

The reactions can be carried out using any of the methods developed for esterifying or aminating carboxylic acids with alcohols or amines. Of these, the methods of H. A. Staab, Angew. Chem. Internat. Edit., (1), 351 (1962) using N,N'-carbonyl diimidazole (CDI) as the acylating agent for esters or amides, and of G. W. Anderson, et al., J. Amer. Chem. Soc. 86, 1839 (1964), using N-Hydroxysuccinimide (NHS) to activate carboxylic acids for amidation were used.

EXAMPLE 13

Preparation of Secondary Derivatives of Functionalized Fibrils

N,N'-Carbonyl Diimidazole

Clean, dry, aprotic solvents (e.g., toluene or dioxane) are required for this procedure. Stoichiometric amounts of reagents are sufficient. For esters, the carboxylic acid compound is reacted in an inert atmosphere (argon) in toluene with a stoichiometric amount of CDI dissolved in toluene at R.T. for 2 hours. During this time, $CO_2$ is evolved. After two hours, the alcohol is added along with catalytic amounts of Na ethoxide and the reaction continued at 80° C. for 4 hr. For normal alcohols, the yields are quantitative. The reactions are:
1.  R—COOH+Im-CO-Im→R—CO-Im+HIm+$CO_2$, Im=Imidazolide, HIm=Imidazole
2.

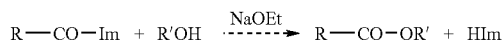

Amidation of amines occurs uncatalyzed at RT. The first step in the procedure is the same. After evolution of $CO_2$, a stoichiometric amount of amine is added at RT and reacted for 1-2 hours. The reaction is quantitative. The reaction is:
3. R—CO-Im+R'$NH_2$→R—CO—NHR+Him N-Hydroxysuccinimide Activation of carboxylic acids for amination with primary amines occurs through the N-hydroxysuccinamyl ester; carbodiimide is used to tie up the water released as a substituted urea. The NHS ester is then converted at RT to the amide by reaction with primary amine. The reactions are:
1. R—COOH+NHS+CDI→R—CONHS+Subst. Urea
2. R—CONHS+R'$NH_2$→R—CO—NHR'

Silylation

Trialkylsilylchlorides or trialkylsilanols react immediately with acidic H according to:
R—COOH+Cl—SiR'$_3$→R—CO—SiR$_{13}$+HCl Small amounts of Diaza-1,1,1-bicyclooctane (DABCO) are used as catalysts. Suitable solvents are dioxane and toluene.

EXAMPLE 14

Preparation of Ester/Alcohol Derivatives from Carboxylic Acid-Functionalized Fibrils The carboxylic acid functionalized fibrils were prepared as in Example 11. The carboxylic acid content was 0.75 meq/g. Fibrils were reacted with a stoichiometric amount of CDI in an inert atmosphere with toluene as solvent at R.T. until $CO_2$ evolution ceased. Thereafter, the slurry was reacted at 80° C. with a 10-fold molar excess of polyethyleneglycol (MW 600) and a small amount of NaOEt as catalyst. After two hours reaction, the fibrils were separated by filtration, washed with toluene and dried at 100° C.

EXAMPLE 15

Preparation of Amide/Amine Derivatives from Carboxylic Acid-Functionalized Fibrils (177-041-1)

0.242 g of chlorate-oxidized fibrils (0.62 meq/g) was suspended in 20 ml anhydrous dioxane with stirring in a 100 ml RB flask fitted with a serum stopper. A 20-fold molar excess of N-Hydroxysuccinimide (0.299 g) was added and allowed to dissolve. This was followed by addition of 20-fold molar excess of 1-ethyl-3-(3-dimethylaminopropyl)-carbodiimide (EDAC) (0.510 g), and stirring was continued for 2 hr at RT. At the end of this period stirring was stopped, and the supernatant aspirated and the solids were washed with anhydrous dioxane and MeOH and filtered on a 0.45 micron polysulfone membrane. The solids were washed with additional MeOH on the filter membrane and vacuum-dried until no further weight reduction was observed. Yield of NHS-activated oxidized fibrils was 100% based on the 6% weight gain observed.

100 µl ethylenediamine (en) was added to 10 ml 0.2 M $NaHCO_3$ buffer. An equivalent volume of acetic acid (HOAc) was added to maintain the pH near 8. NHS-activated oxidized fibrils (0.310 g) was added with vigorous stirring and reacted for 1 hr. An additional 300 µl of en and 300 µl HOAc was added for an additional 10 min. The solution was filtered on 0.45 micron polysulfone membrane and washed successively with $NaHCO_3$ buffer, 1% HCl, DI water and EtOH. The solids were dried under vacuo overnight. The HCl salt was converted back to the free amine by reaction with NaOH (177-046-1) for further analysis and reactions.

ESCA was carried out to quantify the amount of N present on the aminated fibrils (GF/$NH_2$). ESCA analysis of 177-046-1 showed 0.90 at % N (177-059). To further assess how much of this N is present as both accessible and reactive amine groups, a derivative was made by the gas phase reaction with pentafluorobenzaldehyde to produce the corresponding Schiff Base linkages with available primary amine groups. ESCA analysis still showed the 0.91 at % N, as expected, and 1.68 at % F. This translates into a 0.34 at % of N present as reactive primary amine on the aminated fibrils (5 F per pentafluorobenzaldehyde molecule). A level of 0.45 at % N would be expected assuming complete reaction with the free ends of each N. The observed level indicates a very high yield from the reaction of N with NHS-activated fibril and confirms the reactivity of the available free amine groups.

At the level of 0.34 at % N present as free amine calculated from the ESCA data, there would be almost complete coverage of the fibrils by the free amine groups allowing coupling of other materials.

EXAMPLE 16

Preparation of Silyl Derivative from Carboxylic Acid-Functionalized Fibrils

Acid functionalized fibrils prepared as in Example 11 were slurried in dioxane in an inert atmosphere. With stirring, a stoichiometric amount of chlorotriethyl silane was added and reacted for 0.5 hr, after which several drops of a 5% solution of DABCO in dioxane was added. The system was reacted for an additional hour, after which the fibrils were collected by filtration and washed in dioxane. The fibrils were dried at 100° C. in 5" vacuum overnight.

Table 5 summarizes the secondary derivative preparations. The products were analyzed by ESCA for C, O, N, Si and F surface contents.

TABLE V

Summary of Secondary Derivative Preparations

| | | ESCA ANALYSIS, ATOM % | | | | | |
|---|---|---|---|---|---|---|---|
| REACTANT | PENDANT GROUP | S | C | N | O | Si | F |
| As Grown | — | — | 98.5 | — | 1.5 | — | — |
| Chlorate Oxidized | —COOH, C=O, C—OH | — | 92.4 | — | 7.6 | — | — |
| $H_2N$—$C_2H_4$—$NH_2$ | —$CONHC_2H_4NH_2$ | — | 99.10 | 0.90 | — | — | — |
| | —$CONHC_2H_4N$=$OC_6F_5$ | — | 97.41 | 0.91 | — | — | 1.68 |

EXAMPLE 17

Preparation of Silyl Derivative from Carboxylic Acid-Functionalized Fibrils Acid functionalized fibrils prepared as in Example 11 are slurried in dioxane in an inert atmosphere. With stirring, a stoichiometric amount of chlorotriethyl silane is added and reacted for 0.5 hr, after which several drops of a 5% solution of DABCO in dioxane is added. The system is reacted for an additional hour, after which the fibrils are collected by filtration and washed in dioxane. The fibrils are dried at 100° C. in 5" vacuum overnight.

Table VI summarizes the secondary derivative preparations. Products are analyzed by ESCA. The analysis confirms the incorporation of the desired pendant groups. The products are analyzed by ESCA for C, O, N, Si and F surface contents.

TABLE VI

Summary of Secondary Derivative Preparations

| | | ESCA ANALYSIS, ATOM % | | | | | |
|---|---|---|---|---|---|---|---|
| REACTANT | PENDANT GROUP | S | C | N | O | Si | F |
| $CF_3CH_2OH$ | —$COOCH_2CF3$ | | NOT ANALYZED | | | | |
| PolyEG-600 | —CO—($OC_2H_4O$—)H | | NOT ANALYZED | | | | |
| HO—$C_2H_4$—SH | —$COOC_2H4SH$ | | | | | | |
| Cl—$SiEt_3$ | —$COSiEt_3$ | | | | | | |

Sulfonic Acid-Functionalized Fibrils

Aryl sulfonic acids, as prepared in Example 1 can be further reacted to yield secondary derivatives. Sulfonic acids can be reduced to mercaptans by $LiAlH_4$ or the combination of triphenyl phosphine and iodine (March, J. P., p. 1107). They can also be converted to sulfonate esters by reaction with dialkyl ethers, i.e., Fibril--$SO_3H$+R—O—R→Fibril-$SO_2OR$+ROH Fibrils Functionalized by Electrophilic Addition to Oxygen-Free Fibril Surfaces or by Metallization The primary products obtainable by addition of activated electrophiles to oxygen-free fibril surfaces have pendant —COOH, —COCl, —CN, —$CH_2NH_2$, —$CH_2OH$, —$CH_2$-Halogen, or HC=O. These can be converted to secondary derivatives by the following:

Fibril-COOH→see above.
Fibril-COCl (acid chloride)+HO—R—Y→F—COO—R—Y (Sec. 4/5)
Fibril-COCl+$NH_2$—R—Y→F—CONH—R—Y
Fibril-CN+$H_2$→F—$CH_2$—$NH_2$
Fibril-$CH_2NH_2$+HOOC—R—Y→F—$CH_2$NHCO—R—Y
Fibril-$CH_2NH_2$+O=CR—R'Y→F—$CH_2$N=CR—R'—Y
Fibril-$CH_2OH$+O(COR—Y)$_2$→F—$CH_2$OCOR—Y
Fibril-$CH_2OH$+HOOC—R—Y→F—$CH_2$OCOR—Y
Fibril-$CH_2$-Halogen+$Y^-$→F—$CH_2$—Y+$X^-$ $Y^-$=$NCO^-$, —$OR^-$
Fibril-C=O+$H_2N$—R—Y→F—C=N—R—Y Fibrils Functionalized by Adsorption of Polynuclear or Polyheteronuclear Aromatic or Planar Macrocyclic Compounds Dilithium Phthalocyanine: In general, the two $Li^+$ ions are displaced from the phthalocyanine (Pc) group by most metal (particularly multi-valent) complexes. Therefore, displacement of the $Li^+$ ions with a metal ion bonded with non-labile ligands is a method of putting stable functional groups onto fibril surfaces. Nearly all transition metal complexes will displace $Li^+$ from Pc to form a stable, non-labile chelate. The point is then to couple this metal with a suitable ligand.

Cobalt (II) Phthalocyanine

Cobalt (II) complexes are particularly suited for this. $Co^{++}$ ion can be substituted for the two $Li^+$ ions to form a very stable chelate. The $Co^{++}$ ion can then be coordinated to a ligand such as nicotinic acid, which contains a pyridine ring with a pendant carboxylic acid group and which is known to bond preferentially to the pyridine group. In the presence of excess nicotinic acid, Co(II)Pc can be electrochemically oxidized to Co(III)Pc, forming a non-labile complex with the pyridine moiety of nicotinic acid. Thus, the free carboxylic acid group of the nicotinic acid ligand is firmly attached to the fibril surface.

Other suitable ligands are the aminopyridines or ethylenediamine (pendant $NH_2$), mercaptopyridine (SH), or other polyfunctional ligands containing either an amino- or pyridyl-moiety on one end, and any desirable function on the other.

7. 3-Dimensional Structures

The oxidized fibrils are more easily dispersed in aqueous media than unoxidized fibrils. Stable, porous 3-dimensional structures with meso- and macropores (pores >2 nm) are very useful as catalysts or chromatography supports. Since fibrils can be dispersed on an individualized basis, a well-dispersed sample which is stabilized by cross-links allows one to construct such a support. Functionalized fibrils are ideal for this application since they are easily dispersed in aqueous or polar media and the functionality provides cross-link points. Additionally, the functionality provides points to support the catalytic or chromatographic sites. The end result is a rigid, 3-dimensional structure with its total surface area accessible with functional sites on which to support the active agent.

Typical applications for these supports in catalysis include their use as a highly porous support for metal catalysts laid down by impregnation, e.g., precious metal hydrogenation catalysts. Moreover, the ability to anchor molecular catalysts by tether to the support via the functionality combined with the very high porosity of the structure allows one to carry out homogeneous reactions in a heterogeneous manner. The tethered molecular catalyst is essentially dangling in a continuous liquid phase, similar to a homogeneous reactor, in which it can make use of the advantages in selectivities and rates that go along with homogeneous reactions. However, being tethered to the solid support allows easy separation and recovery of the active, and in many cases, very expensive catalyst.

These stable, rigid structures also permits carrying out heretofore very difficult reactions, such as asymmetric syntheses or affinity chromatography by attaching a suitable enantiomeric catalyst or selective substrate to the support. Derivatization through Metallo-Pc or Metallo-porphyrin complexes also allows for retrieval of the ligand bonded to the metal ion, and furthermore, any molecule which is bonded to the ligand through the secondary derivatives. For example, in the case where the 3-dimensional structure of functionalized fibrils is an electrode, or part of an electrode, and the functionalization has resulted from adsorption of Co(II)Pc, electrochemical oxidation of Co(II) to Co(III) in the presence of nicotinic acid will produce a non-labile Co(III)-pyridyl complex with a carboxylic acid as the pendent group. Attaching a suitable antigen, antibody, catalytic antibody, or other site-specific trapping agent will permit selective separations of molecules (affinity chromatography) which are otherwise very difficult to achieve. After washing the electrode to remove occluded material, the Co(III) complex containing the target molecule can be electrochemically reduced to recover the labile Co(II) complex. The ligand on Co(II) containing the target molecule can then be recovered by mass action substitution of the labile Co(II) ligand, thereby effecting a separation and recovery of molecules which are otherwise very difficult or expensive to perform (e.g., chiral drugs).

Another example of 3-dimensional structures are fibril-ceramic composites.

EXAMPLE 18

Preparation of Alumina-Fibril Composites
(185-02-01)

One g of nitric acid oxidized fibrils (185-01-02) was highly dispersed in 100 cc DI water using and U/S disintegrator. The fibril slurry was heated to 90° C. and a solution of 0.04 mol aluminum tributoxide dissolved in 20 cc propanol was slowly added. Reflux was continued for 4 hr, after which the condenser was removed to drive out the alcohol. After 30 min the condenser was put back and the slurry refluxed at 100° C. overnight. A black sol with uniform appearance was obtained. The sol was cooled to RT and after one week, a black gel with a smooth surface was formed. The gel was heated at 300° C. in air for 12 hr.

The alumina-fibril composites were examined by SEM. Micrographs of cracked surfaces showed a homogeneous dispersion of fibrils in the gel.

EXAMPLE 19

Preparation of Silica-Fibril Composites (173-85-03)

Two g of nitric acid oxidized fibrils (173-83-03) were highly dispersed on 200 cc ethanol using ultrasonification. A solution of 0.1 mol tetraethoxysilane dissolved in 50 cc ethanol was slowly added to the slurry at RT, followed by 3 cc conc. HCL. The mixture was heated to 85° C. and maintained at that temperature until the volume was reduced to 100 cc. The mixture was cooled and set aside until it formed a black solid gel. The gel was heated at 300° C. in air.

The silica-fibril composites were examined by SEM. Micrographs of cracked surfaces showed a homogeneous dispersion of fibrils in the gel.

Similar preparations with other ceramics, such as zirconia, titania, rare earth oxides as well as ternary oxides can be prepared.

As illustrated by the foregoing description and examples, the invention has application in the formulation of a wide variety of functionalized nanotubes.

The terms and expressions which have been employed are used as terms of description and not of limitations, and there is no intention in the use of such terms or expressions of excluding any equivalents of the features shown and described as portions thereof, its being recognized that various modifications are possible within the scope of the invention.

What is claimed is:

1. A method of uniformly substituting the surface of carbon fibrils with a functional group comprising
   chemically reacting non-oxidized carbon fibrils with an effective amount of a reactant capable of uniformly substituting surface carbon atoms with the same functional groups onto the surface of said carbon fibrils;
   wherein chemically reacting comprises a reaction selected from the group consisting of sulfonation, electrophilic addition, and metallation.

2. A method of uniformly substituting the surface of carbon fibrils with a functional group as claimed in claim 1, wherein the functional group carboxyl comprises a moiety.

3. The method of claim 1, wherein the reaction comprises sulfonation.

4. The method of claim 3, wherein the reactant comprises $SO_3$.

5. The method of claim 1, wherein the reaction comprises electrophilic addition.

6. The method of claim 5, wherein the reactant is selected from the group consisting of:
   $CH_2=CHCOX$ where X is —OH, —Cl, —$NH_2$, or —H;
   maleic anhydride;
   maleic acid;
   cyanogen;
   $CH_2=CH—CH_2Y$ where Y is —$NH_2$, —OH, or -halogen;
   $H_2O$; and
   $CH_2=CH—CN$.

7. The method of claim 5, wherein the method comprises:
   heating the carbon fibrils while purging with an inert gas; and
   keeping the carbon fibrils under an inert atmosphere while cooling.

8. The method of claim 6, wherein the method comprises:
   heating the carbon fibrils while purging with an inert gas; and
   keeping the carbon fibrils under an inert atmosphere while cooling.

9. The method of claim 1, wherein the reaction comprises metallation.

10. The method of claim 9, wherein the reactant comprises a metal selected from the group consisting of Li, Be, Mg, Al, and Tl.

11. The method of claim 9, wherein the method comprises:
    heating the carbon fibrils while purging with hydrogen gas; and
    keeping the carbon fibrils under hydrogen gas while cooling.

12. The method of claim 10, wherein the method comprises:
    heating the carbon fibrils while purging with hydrogen gas; and
    keeping the carbon fibrils under hydrogen gas while cooling.

* * * * *

UNITED STATES PATENT AND TRADEMARK OFFICE
CERTIFICATE OF CORRECTION

| | | |
|---|---|---|
| PATENT NO. | : 7,854,945 B2 | Page 1 of 1 |
| APPLICATION NO. | : 11/412350 | |
| DATED | : December 21, 2010 | |
| INVENTOR(S) | : Fischer et al. | |

It is certified that error appears in the above-identified patent and that said Letters Patent is hereby corrected as shown below:

Column 22, Line 26 (Claim 2, line 3): change "the functional group carboxyl comprises a moiety." to -- the functional group comprises a carboxyl moiety. --

Signed and Sealed this
Twenty-second Day of February, 2011

David J. Kappos
*Director of the United States Patent and Trademark Office*